US011207072B2

(12) United States Patent
Prior

(10) Patent No.: US 11,207,072 B2
(45) Date of Patent: Dec. 28, 2021

(54) BUTTRESS FIXATION FOR A CIRCULAR STAPLER

(71) Applicant: Covidien LP, Mansfield, MA (US)

(72) Inventor: Scott J. Prior, Shelton, CT (US)

(73) Assignee: COVIDIEN LP, Mansfield, MA (US)

(*) Notice: Subject to any disclaimer, the term of this patent is extended or adjusted under 35 U.S.C. 154(b) by 242 days.

(21) Appl. No.: 16/410,355

(22) Filed: May 13, 2019

(65) Prior Publication Data
US 2019/0269409 A1 Sep. 5, 2019

Related U.S. Application Data

(63) Continuation of application No. 14/875,865, filed on Oct. 6, 2015, now Pat. No. 10,285,704, which is a continuation of application No. 13/648,703, filed on Oct. 10, 2012, now Pat. No. 9,161,753.

(51) Int. Cl.
| A61B 17/068 | (2006.01) |
| A61B 17/072 | (2006.01) |
| A61B 17/10 | (2006.01) |
| A61B 17/115 | (2006.01) |

(52) U.S. Cl.
CPC ........ *A61B 17/1155* (2013.01); *A61B 17/068* (2013.01); *A61B 17/07292* (2013.01); *A61B 17/105* (2013.01)

(58) Field of Classification Search
CPC .............................................. A61B 17/07292
USPC ...................................................... 227/176.1
See application file for complete search history.

(56) References Cited

U.S. PATENT DOCUMENTS

| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |

(Continued)

FOREIGN PATENT DOCUMENTS

| CA | 2282761 A1 | 9/1998 |
| DE | 1602563 U | 3/1950 |

(Continued)

OTHER PUBLICATIONS

Chinese First Office Action corresponding to counterpart Int'l Appln. No. CN 2013107068710 dated Dec. 16, 2016.

(Continued)

*Primary Examiner* — Thanh K Truong
*Assistant Examiner* — Patrick B Fry

(57) ABSTRACT

A stapling apparatus includes a body portion, a staple cartridge disposed within the body portion, and a buttress removably attached to the staple cartridge. The staple cartridge includes a plurality of staple receiving slots defined in a tissue contacting surface of the staple cartridge, with each staple receiving slot of the plurality of staple receiving slots including a staple disposed therein. The buttress includes a plurality of tabs at an outer edge of the buttress. The buttress is releasably retained on the staple cartridge by at least one tab of the plurality of tabs extending into a staple receiving slot of the plurality of staple receiving slots defined in the staple cartridge.

9 Claims, 4 Drawing Sheets

(56) References Cited

U.S. PATENT DOCUMENTS

| | | |
|---|---|---|
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 * | 7/2003 | Grant .............. A61B 17/072 606/151 |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |

(56) References Cited

U.S. PATENT DOCUMENTS

| | | | |
|---|---|---|---|
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,407,075 B2 * | 8/2008 | Holsten | A61B 17/1114 227/175.1 |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 * | 6/2009 | Bauman | A61B 17/072 227/175.1 |
| 7,559,937 B2 | 7/2009 | de la Torre et al. |
| 7,571,845 B2 | 8/2009 | Viola |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 * | 12/2010 | Marczyk | A61B 17/07207 227/175.1 |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 * | 4/2013 | Racenet | A61B 17/07207 227/180.1 |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,615,856 B1 * | 12/2013 | Gelbart | B21F 25/00 29/7.1 |
| 8,616,430 B2 | 12/2013 | Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |

(56) References Cited

U.S. PATENT DOCUMENTS

| | | | |
|---|---|---|---|
| 8,899,464 B2* | 12/2014 | Hueil | A61B 17/0644 227/176.1 |
| 8,920,443 B2 | 12/2014 | Hiles et al. | |
| 8,920,444 B2 | 12/2014 | Hiles et al. | |
| 8,939,344 B2 | 1/2015 | Olson et al. | |
| 8,967,448 B2 | 3/2015 | Carter et al. | |
| 9,005,243 B2 | 4/2015 | Stopek et al. | |
| 9,010,606 B2 | 4/2015 | Aranyi et al. | |
| 9,010,608 B2 | 4/2015 | Casasanta, Jr. et al. | |
| 9,010,609 B2 | 4/2015 | Carter et al. | |
| 9,010,610 B2 | 4/2015 | Hodgkinson | |
| 9,010,612 B2 | 4/2015 | Stevenson et al. | |
| 9,016,543 B2 | 4/2015 | (Prommersberger) Stopek et al. | |
| 9,016,544 B2 | 4/2015 | Hodgkinson | |
| 9,027,817 B2 | 5/2015 | Milliman et al. | |
| 9,044,227 B2 | 6/2015 | Shelton, IV et al. | |
| 9,055,944 B2 | 6/2015 | Hodgkinson et al. | |
| 9,084,602 B2 | 7/2015 | Gleiman | |
| 9,107,665 B2 | 8/2015 | Hodgkinson et al. | |
| 9,107,667 B2 | 8/2015 | Hodgkinson | |
| 9,113,871 B2 | 8/2015 | Milliman et al. | |
| 9,113,873 B2 | 8/2015 | Marczyk et al. | |
| 9,113,885 B2 | 8/2015 | Hodgkinson et al. | |
| 9,113,893 B2 | 8/2015 | Sorrentino et al. | |
| 9,161,753 B2 | 10/2015 | Prior | |
| 9,161,757 B2 | 10/2015 | Bettuchi | |
| 9,186,140 B2 | 11/2015 | Hiles et al. | |
| 9,186,144 B2 | 11/2015 | Stevenson et al. | |
| 9,192,378 B2 | 11/2015 | Aranyi et al. | |
| 9,192,379 B2 | 11/2015 | Aranyi et al. | |
| 9,192,380 B2 | 11/2015 | (Tarinelli) Racenet et al. | |
| 9,192,383 B2 | 11/2015 | Milliman | |
| 9,192,384 B2 | 11/2015 | Bettuchi | |
| 9,198,660 B2 | 12/2015 | Hodgkinson | |
| 9,198,663 B1 | 12/2015 | Marczyk et al. | |
| 9,204,881 B2 | 12/2015 | Penna | |
| 9,220,504 B2 | 12/2015 | Viola et al. | |
| 9,226,754 B2 | 1/2016 | D'Agostino et al. | |
| 9,237,892 B2 | 1/2016 | Hodgkinson | |
| 9,237,893 B2 | 1/2016 | Carter et al. | |
| 9,277,922 B2 | 3/2016 | Carter et al. | |
| 9,295,466 B2 | 3/2016 | Hodgkinson et al. | |
| 9,326,773 B2 | 5/2016 | Casasanta, Jr. et al. | |
| 9,328,111 B2 | 5/2016 | Zhou et al. | |
| 9,345,479 B2 | 5/2016 | (Tarinelli) Racenet et al. | |
| 9,351,729 B2 | 5/2016 | Orban, III et al. | |
| 9,351,731 B2 | 5/2016 | Carter et al. | |
| 9,351,732 B2 | 5/2016 | Hodgkinson | |
| 9,358,005 B2 | 6/2016 | Shelton, IV et al. | |
| 9,364,229 B2 | 6/2016 | D'Agostino et al. | |
| 9,364,234 B2 | 6/2016 | (Prommersberger) Stopek et al. | |
| 9,402,627 B2 | 8/2016 | Stevenson et al. | |
| 9,414,839 B2 | 8/2016 | Penna | |
| 9,433,412 B2 | 9/2016 | Bettuchi et al. | |
| 9,433,413 B2 | 9/2016 | Stopek | |
| 9,433,420 B2 | 9/2016 | Hodgkinson | |
| 9,445,812 B2 | 9/2016 | Olson et al. | |
| 9,445,817 B2 | 9/2016 | Bettuchi | |
| 9,486,215 B2 | 11/2016 | Olson et al. | |
| 9,504,470 B2 | 11/2016 | Milliman | |
| 9,572,576 B2 | 2/2017 | Hodgkinson et al. | |
| 9,597,077 B2 | 3/2017 | Hodgkinson | |
| 9,610,080 B2 | 4/2017 | Whitfield et al. | |
| 9,622,745 B2 | 4/2017 | Ingmanson et al. | |
| 9,629,626 B2 | 4/2017 | Soltz et al. | |
| 9,655,620 B2 | 5/2017 | Prescott et al. | |
| 9,675,351 B2 | 6/2017 | Hodgkinson et al. | |
| 9,681,936 B2 | 6/2017 | Hodgkinson et al. | |
| 9,693,772 B2 | 7/2017 | Ingmanson et al. | |
| 9,775,617 B2 | 10/2017 | Carter et al. | |
| 9,775,618 B2 | 10/2017 | Bettuchi et al. | |
| 9,782,173 B2 | 10/2017 | Mozdzierz | |
| 9,844,378 B2 | 12/2017 | Casasanta et al. | |
| 9,931,116 B2 | 4/2018 | Racenet et al. | |
| 10,022,125 B2 | 7/2018 | (Prommersberger) Stopek et al. | |
| 10,285,704 B2 | 5/2019 | Prior | |
| 2002/0028243 A1 | 3/2002 | Masters | |
| 2002/0086990 A1 | 7/2002 | Kumar et al. | |
| 2002/0091397 A1 | 7/2002 | Chen | |
| 2002/0151911 A1 | 10/2002 | Gabbay | |
| 2002/0165559 A1 | 11/2002 | Grant et al. | |
| 2002/0165563 A1 | 11/2002 | Grant et al. | |
| 2003/0065345 A1 | 4/2003 | Weadock | |
| 2003/0078209 A1 | 4/2003 | Schmidt | |
| 2003/0083676 A1 | 5/2003 | Wallace | |
| 2003/0120284 A1 | 6/2003 | Palacios et al. | |
| 2003/0125676 A1 | 7/2003 | Swenson et al. | |
| 2003/0181927 A1 | 9/2003 | Wallace | |
| 2003/0183671 A1 | 10/2003 | Mooradian et al. | |
| 2003/0196668 A1 | 10/2003 | Harrison et al. | |
| 2003/0208231 A1 | 11/2003 | Williamson et al. | |
| 2004/0092912 A1 | 5/2004 | Jinno et al. | |
| 2004/0093029 A1 | 5/2004 | Zubik et al. | |
| 2004/0107006 A1 | 6/2004 | Francis et al. | |
| 2004/0131418 A1 | 7/2004 | Budde et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0131225 A1 | 6/2005 | Kumar et al. | |
| 2005/0143756 A1 | 6/2005 | Jankowski | |
| 2005/0149073 A1 | 7/2005 | Arani et al. | |
| 2005/0154093 A1 | 7/2005 | Kwon et al. | |
| 2005/0228446 A1 | 10/2005 | Mooradian et al. | |
| 2005/0245965 A1 | 11/2005 | Orban, III et al. | |
| 2005/0283256 A1 | 12/2005 | Sommerich et al. | |
| 2006/0004407 A1 | 1/2006 | Hiles et al. | |
| 2006/0008505 A1 | 1/2006 | Brandon | |
| 2006/0025816 A1 | 2/2006 | Shelton | |
| 2006/0085030 A1 | 4/2006 | Bettuchi et al. | |
| 2006/0085034 A1* | 4/2006 | Bettuchi | A61B 17/1155 606/219 |
| 2006/0093672 A1 | 5/2006 | Kumar et al. | |
| 2006/0121266 A1 | 6/2006 | Fandel et al. | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0190027 A1 | 8/2006 | Downey | |
| 2006/0219752 A1 | 10/2006 | Arad et al. | |
| 2006/0271104 A1 | 11/2006 | Viola et al. | |
| 2007/0026031 A1 | 2/2007 | Bauman et al. | |
| 2007/0034669 A1 | 2/2007 | de la Torre et al. | |
| 2007/0049953 A2 | 3/2007 | Shimoji et al. | |
| 2007/0054880 A1 | 3/2007 | Saferstein et al. | |
| 2007/0114262 A1 | 5/2007 | Mastri et al. | |
| 2007/0123839 A1 | 5/2007 | Rousseau et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2007/0213522 A1 | 9/2007 | Harris et al. | |
| 2007/0237741 A1 | 10/2007 | Figuly et al. | |
| 2007/0237742 A1 | 10/2007 | Figuly et al. | |
| 2007/0243227 A1 | 10/2007 | Gertner | |
| 2007/0246505 A1 | 10/2007 | Pace-Floridia et al. | |
| 2008/0009811 A1 | 1/2008 | Cantor | |
| 2008/0029570 A1 | 2/2008 | Shelton et al. | |
| 2008/0082126 A1 | 4/2008 | Murray et al. | |
| 2008/0110959 A1* | 5/2008 | Orban | A61B 17/068 227/176.1 |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1* | 7/2008 | Bauman | A61B 17/072 606/148 |
| 2008/0164440 A1 | 7/2008 | Maase et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |

(56) References Cited

U.S. PATENT DOCUMENTS

| | | |
|---|---|---|
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Farinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1* | 8/2009 | Huitema ............... A61B 50/30 227/176.1 |
| 2009/0218384 A1 | 9/2009 | Aranyi |
| 2009/0220560 A1 | 9/2009 | Wan et al. |
| 2009/0263441 A1 | 10/2009 | McKay |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0016888 A1 | 1/2010 | Calabrese et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0087840 A1 | 4/2010 | Ebersole et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089220 A1 | 4/2011 | Ingmanson et al. |
| 2011/0089375 A1 | 4/2011 | Chan et al. |
| 2011/0125138 A1 | 5/2011 | Malinouskas et al. |
| 2011/0166673 A1 | 7/2011 | Patel et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0156289 A1 | 6/2012 | Blaskovich et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241499 A1 | 9/2012 | Baxter, III et al. |
| 2012/0253298 A1 | 10/2012 | Henderson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0146641 A1 | 6/2013 | Shelton, IV et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0193186 A1 | 8/2013 | (Tarinelli) Racenet et al. |
| 2013/0193192 A1 | 8/2013 | Casasanta, Jr. et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256377 A1 | 10/2013 | Schmid et al. |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0097224 A1 | 4/2014 | Prior |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |

(56) References Cited

U.S. PATENT DOCUMENTS

| | | |
|---|---|---|
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2090244 A2 | 8/2009 |
| EP | 2491867 A1 | 8/2012 |
| EP | 2497431 A1 | 9/2012 |
| EP | 2620106 A2 | 7/2013 |
| JP | 2000166933 A | 6/2000 |
| JP | 2002202213 A | 7/2002 |
| JP | 2007124166 A | 5/2007 |
| WO | 9005489 A1 | 5/1990 |
| WO | 95/16221 A1 | 6/1995 |
| WO | 98/38923 A1 | 9/1998 |
| WO | 93082126 A1 | 10/2003 |
| WO | 2008109125 A1 | 9/2008 |
| WO | 2010075298 A2 | 7/2010 |

OTHER PUBLICATIONS

Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appin. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Chinese Notification of Reexamination corresponding to counterpart Int'l Appln. No. CN 201010517292.8 dated Jun. 2, 2015.
Extended European Search Report corresponding to counterpart Int'l Appln No. EP 14 15 2060.1 dated Aug. 14, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16150232.3, dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.

(56) References Cited

OTHER PUBLICATIONS

European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035 0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013I; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.

(56) References Cited

OTHER PUBLICATIONS

Australian Examination Report No. 1 corresponding to counterpart Australian Appln. No. AU 2014200793 dated Sep. 2, 2017.
Australian Patent Examination Report No. 1 corresponding to counterpart Int'l Appln No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln No. AU 2012261752 dated Sep. 3, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
European Office Action corresponding to counterpart Int'l Appln. No. EP 15 18 3819.0 dated Mar. 27, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Chinese Office Action corresponding to counterpart Int'l Appln No. CN 201210129787.2 dated Aug. 24, 2015.
Extended European Search Report corresponding to EP 15 18 3819.0 dated Dec. 11, 2015.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).

* cited by examiner

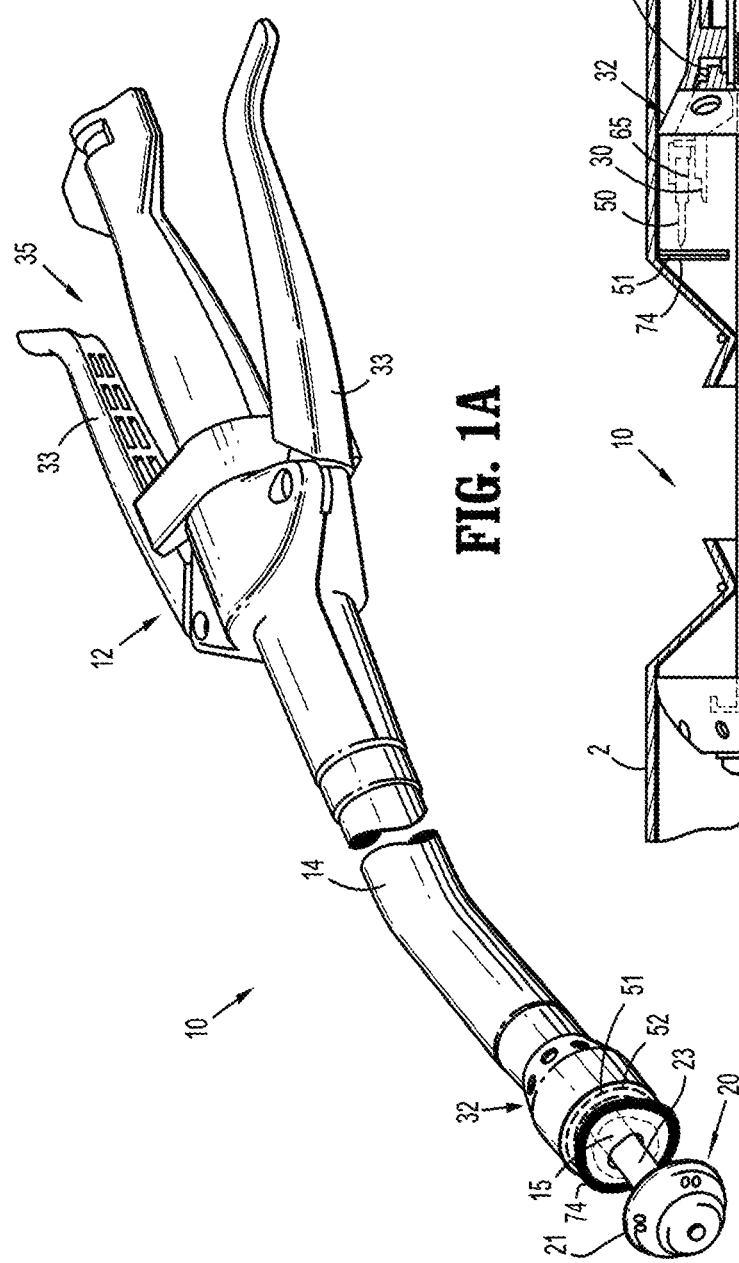
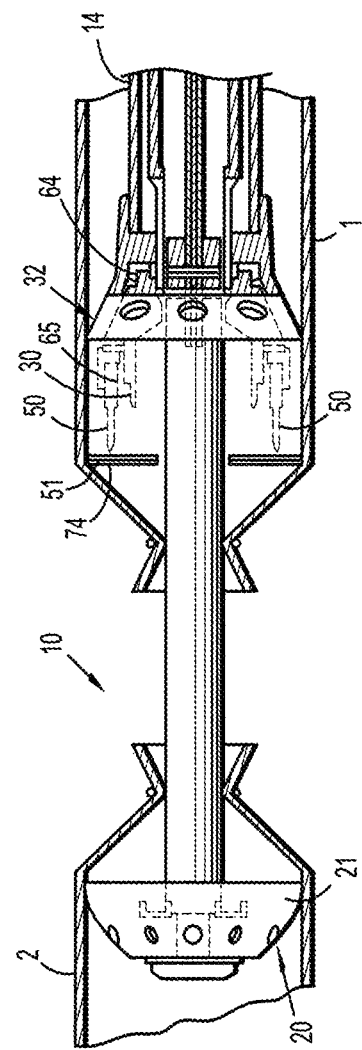
FIG. 1A
FIG. 1B

BUTTRESS FIXATION FOR A CIRCULAR STAPLER

CROSS REFERENCE TO RELATED APPLICATIONS

This application is a continuation of U.S. patent application Ser. No. 14/875,865, filed Oct. 6, 2015, which is a continuation of U.S. patent application Ser. No. 13/648,703, filed Oct. 10, 2012 (now U.S. Pat. No. 9,161,753), the entire contents of each of which are incorporated herein by reference.

TECHNICAL FIELD

The present application relates to surgical stapling apparatus and, in particular, surgical stapling apparatus having a buttress releasably fixed thereto.

BACKGROUND

Attaching surgical buttresses or staple line reinforcement materials to surgical staplers is known. Trumbull et al., U.S. Pat. No. 5,263,629, the disclosure of which is hereby incorporated by reference herein in its entirety, discloses an absorbent and bioabsorbable pledget material attached to a surgical stapler. Buttresses used in conjunction with a tubular sleeve have been proposed. For example, U.S. Pat. No. 5,503,638 to Cooper et al., the entire disclosure of which is hereby incorporated by reference herein, proposes a tubular sleeve dimensioned to fit over and closely surround the jaws of a stapler. The sleeve can be made from non-woven polyethylene attached to a strip of material made from animal tissue.

McKean et al., U.S. Pat. No. 5,542,594, the entire disclosure of which is hereby incorporated by reference herein, discloses a stapling apparatus having biocompatible fabric releasably attached thereto. The fabric can be tubular in configuration for attachment to the stapling apparatus, or can be attached using pins.

Tarinelli et al., International Publication No. WO 08/109125, the entire disclosure of which is hereby incorporated by reference herein, discloses an anchor, or a suture material, for attaching a buttress, which is released when the anchor, or suture, is cut by a knife.

Mooradian et al., WO 03/082126, the entire disclosure of which is hereby incorporated by reference herein, discloses a circular stapling apparatus having a buttress material positioned on the staple cartridge and/or anvil. The buttress material may be preformed so as to have a raised central region so that it can be positioned on the staple cartridge and/or anvil.

There is a need for reliable methods of removably attaching a staple line reinforcement material or buttress material onto a circular stapling apparatus, or other stapling apparatus, so that the material does not interfere with the operation of the apparatus, remains on the apparatus until after the staples are fired, and is convenient and easy to install and use.

SUMMARY

In an aspect of the present disclosure, a circular stapling apparatus has an anvil assembly with an anvil member and a shaft, and a tubular body portion. The shaft of the anvil assembly is connectable to the tubular body portion so that the anvil assembly is movable toward and away from the tubular body portion. A buttress material is removably attached to the anvil assembly, staple cartridge, or both, by at least one anchor, at least one of the anvil assembly and staple cartridge have a notch shaped for retaining the anchor thereto.

The apparatus has a pusher with a fingers for driving the staples. At least one of the fingers includes a protrusion. At least one of the anvil assembly and staple cartridge has a notch shaped for retaining the anchor, the pusher being movable to move the protrusion into engagement with the anchor in the notch.

The anchor may be a length of suture. The apparatus may further comprise adhesive. The apparatus may further comprise a fastener holding the anchor and being positioned adjacent the notch. In certain embodiments, the notch pinches the anchor. The notch can be defined in a tissue contacting surface of the at least one of the anvil assembly and staple cartridge. The notch may communicate with a staple receiving recess of the staple cartridge. The notch may communicate with a staple forming recess of the anvil member.

In certain embodiments, the notch has a first portion and a second portion, the first portion being smaller in dimension than the diameter of the anchor, and the second portion being bigger than the first portion.

The buttress material can define features selected from the group consisting of slits and perforations. The buttress material can define slits that extend from an outer edge thereof. The protrusion may cut the anchor.

BRIEF DESCRIPTION OF THE DRAWINGS

Embodiments of the presently disclosed surgical device are disclosed herein, with reference to the following drawings:

FIG. 1A is a perspective view of a stapling instrument in accordance with an embodiment of the present disclosure;

FIG. 1B is a partial cross-sectional view of the stapling instrument shown in FIG. 1A;

DETAILED DESCRIPTION

Figure 2A:
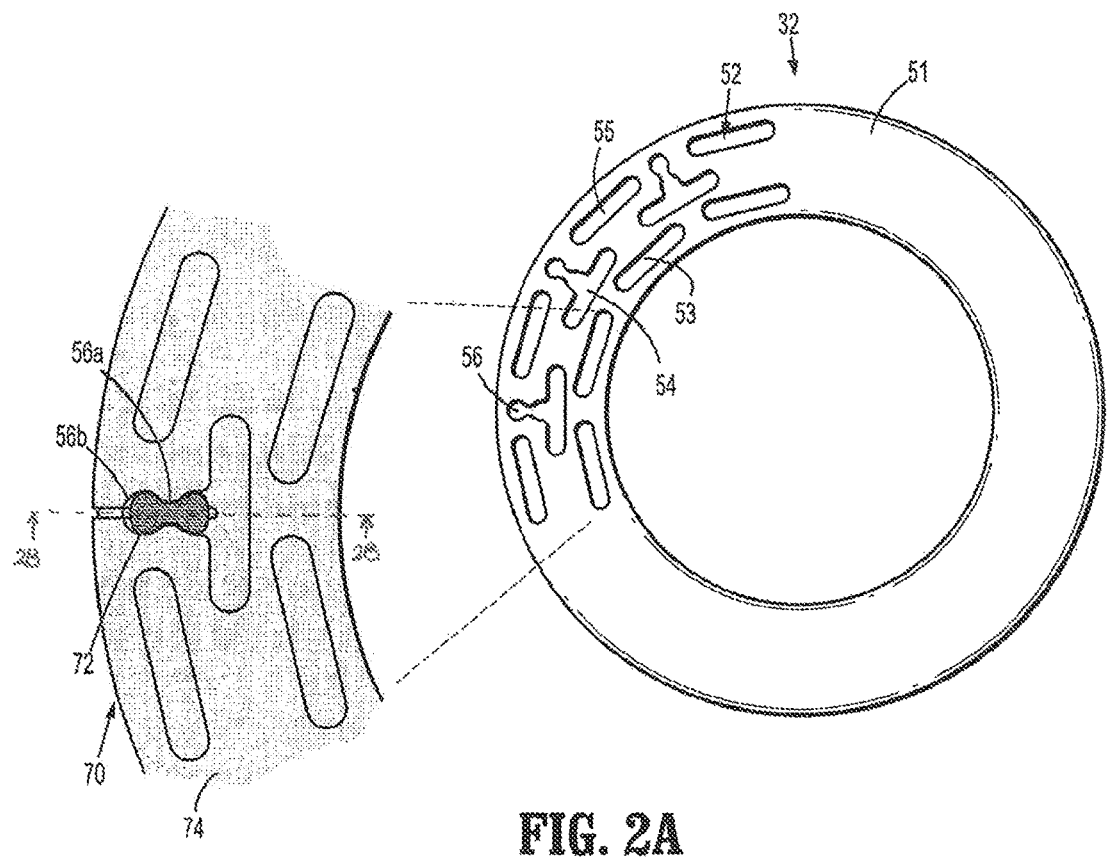
FIG. 2A is a top plan view of a staple cartridge, and a detailed view of a portion thereof, in accordance with an embodiment of the present disclosure.

Persons having skill in the art will understand the present invention from reading the following description in conjunction with the accompanying drawings. Reference characters indicate the same or similar elements throughout the drawings. As is customary, the term "distal" refers to a location farther from the user of the instrument and the term "proximal" refers to a location that is closer to the user of the instrument.

A circular stapling instrument or apparatus (also referred to herein as a stapler) 10 is shown in FIGS. 1A-1B and has a handle portion 12, a tubular body portion 14, and an anvil assembly 20. The anvil assembly 20 is at the distal end of the instrument 10, and is movable toward and away from the tubular body portion 14. The handle portion 12 has at least one movable handle 33 for actuating the firing of staples 50 and the cutting of tissue 1, 2. A knob 35 is at the proximal end of the handle portion 12 and can be turned to move the anvil assembly 20 toward the tubular body portion 14 or away from the tubular body portion 14. A buttress 74 is shown generally disposed around the shaft 23.

Although a circular stapling apparatus is described in detail herein, in any of the embodiments disclosed herein, the stapling apparatus may be a linear endoscopic stapler, a linear stapler for open surgery, a transverse surgical stapler, or other surgical device. Circular staplers are disclosed in U.S. Pat. No. 5,915,616, the disclosure of which is hereby incorporated by reference in its entirety. Endoscopic staplers are disclosed in U.S. Pat. Nos. 6,330,965 and 6,241,139, the disclosures of which are hereby incorporated by reference in their entirety. Transverse surgical staplers are disclosed in U.S. Pat. No. 5,964,394, the disclosure of which is hereby incorporated by reference in its entirety. U.S. Pat. No. 7,334,717, the disclosure of which is hereby incorporated by reference in its entirety, discloses a stapler intended for open surgical procedures.

The tubular body portion 14 can be flexible, straight or curved, or otherwise configured for the surgical procedure. The distal end of the tubular body portion 14 has a staple cartridge 32 disposed therein. The staple cartridge 32 has a circular array of staple retaining or receiving slots 52 defined in a tissue contacting surface 51 of the staple cartridge 32. The anvil assembly 20 has an anvil member 21 with a circular array of staple forming recesses that correspond to the staple retaining or receiving slots 52. The anvil assembly 20 also has a shaft 23 that connects with a rod 15 in the tubular body portion 14.

A staple pusher 64 is disposed in the staple cartridge 32 and has a plurality of fingers or pushers 65 that are aligned with the staple receiving slots 52. The staple pusher 64 is a conical member that is disposed in the staple cartridge 32. The staple pusher 64 is movable in the distal direction to drive the staples 50 out of the staple cartridge 32 and toward the staple forming recesses in the anvil member 21. There are three circular rows of staples that are driven into tissue, as shown in FIG. 2. A knife 30 has a cylindrical shape and is disposed radially inwardly of the pushers 65. The knife 30 is mounted to a surface of the staple pusher 64 so that after the staples 50 are driven through tissue 1, 2 and into the staple forming recesses, the tissue radially interior to the circular rows of staples is cut. The staple cartridge 32 can be a removable and replaceable assembly so that the rest of the circular stapling apparatus 10 can be re-sterilized and reused, or the circular stapling apparatus 10 can be reused on the same patient without re-sterilization.

The rod 15 inside the tubular body portion 14 extends proximally through the apparatus 10 to the knob 35. The distal end of the knob 35 is attached to a member that has a helical groove defined on a surface thereof. A pin attached to a proximal end of the rod 15 is disposed in the groove so that, as the knob 35 is rotated, the pin travels in the groove, moving the rod 15 in a distal or proximal direction. The anvil shaft 23, which is attached to the rod 15, is also moved, moving the anvil assembly 20 toward or away from the tubular body portion 14. When the knob 35 is rotated in a first direction, the anvil assembly 20 is moved away from the tubular body portion 14, allowing tissue to be placed between the anvil assembly 20 and the tissue contacting surface 51 of the staple cartridge 32. When the knob 35 is rotated in a second direction, the anvil assembly 20 is moved toward the tubular body portion 14, allowing the tissue to be clamped between the staple cartridge 32 and anvil assembly 20. Other means of moving the anvil assembly with respect to the tubular body portion are contemplated. It is also contemplated, in any of the embodiments disclosed herein, that the instrument 10 can be connected to a motorized assembly. For example, a motorized assembly can be provided in the handle portion 12, and power can be supplied from external sources, or from a battery provided in the handle portion 12.

The pivotable handle or handles 33 can be connected to a tubular member or pair of bands that are attached to the staple pusher 64 by, for example, linkages or the like. In this way, when the handle or handles 33 are depressed, the tubular member or bands are advanced, advancing the staple pusher 64, driving the staples 50 through tissue 1, 2 and against the anvil member 21, and advancing the knife 30 to cut tissue radially inward of the rows of surgical staples 50.

Figure 2B:
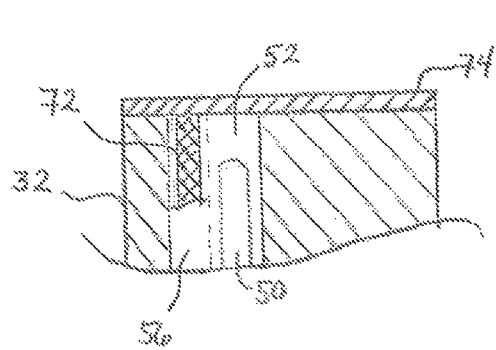
FIG. 2B is a cross-sectional view of the staple cartridge of FIG. 2A, taken along line 2B-2B of FIG. 2A.

As shown in FIGS. 2A and 2B, a buttress fixation system 70 is provided on the staple cartridge 32. The staple cartridge 32 has a plurality of staple receiving slots 52 defined in a tissue contacting surface 51 therein. Only a portion of the staple receiving slots 52 are shown in FIG. 2A, but it is understood that the rows of staple receiving slots 52 extend all the way around the circular face of the staple cartridge 32. The staple receiving slots 52 have an inner row 53, middle row 54, and an outer row 55. The middle row 54 of staple receiving slots 52 includes at least one notch 56 extending outwardly away from the rod 15 of the apparatus. This at least one notch 56 receives an anchor 72, which is a strap, cable, wire, thread, strand, or the like, which can be for example, a length of suture 72. The notch 56 is configured to have a shape that pinches the length of suture 72. For example, the notch 56 will have a first portion 56a with a first dimension, and a second portion 56b with a second dimension. The first dimension is smaller than the diameter, or cross-sectional dimension, of the length of suture 72, so that the length of suture 72 is retained in the notch 56. The second dimension is bigger than the first dimension, allowing the length of suture 72 to move out of the notch 56. In any of the embodiments disclosed herein, the notch 56 can have a shape like the number 8, the shape of the letter V, or any shape for retaining and releasing the anchor, or suture.

The anchor 72, which can be a strap, cable, wire, thread, strand, suture, or the like, is desirably a bioabsorbable suture, which can be made from polyglycolic acid, glycolide trimethylene carbonate, polylactic acid, or any of the bioabsorbable materials from which sutures, buttress materials, and other medical implants, can be made. Animal derived materials, which are known in the art, are also contemplated for the buttress and/or anchor. In any of the embodiments disclosed herein, the suture can be a material that is not bioabsorbable. In certain embodiments, the anchor 72 is attached to the stapler 10 and removed with the stapler 10 after the staples 50 have been fired. In certain embodiments, the anchor 72 is bioabsorbable and is attached to the buttress 74, or is formed as part of the buttress 74, and is left in the body of the patient. Alternatively, the surgeon can trim the anchor or anchors 72 during surgery.

Figure 3:
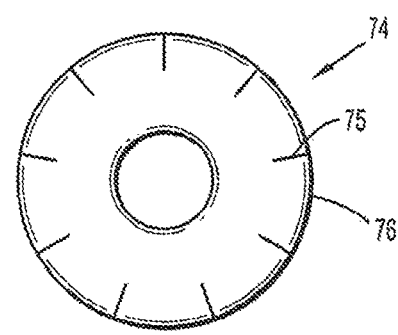
FIG. 3 is a top plan view of a surgical buttress in accordance with an embodiment of the present disclosure.

The length of suture 72 can be attached to the buttress 74 by welding, or using an adhesive, or by heat pressing, or any known method. Alternatively, the length of suture 72 can be integrally formed with the buttress 74, as an extension thereof. For example, the buttress 74 can be formed as a circular disc, as shown in FIG. 3, and can have straps that extend from the outer edge 76 thereof. The straps can separate from the buttress 74 at perforations, or by virtue of the bioabsorbability of the material. For example, the straps can be made much thinner than the buttress 74. In another example, the straps or length of suture 72 can be trimmed by the surgeon after the staples 50 are fired and the stapling instrument 10 is removed from the site. The anchor 72 or anchors 72 can be one or more lengths of suture material. That is, the anchor 72 can be a single piece of suture, portions of which extending into the notch or notches 56 to retain the buttress 74. In any of the embodiments disclosed herein, the anchor 72 comprises a plurality or pieces of suture material that extend into corresponding notches 56.

In any of the embodiments disclosed herein, a fastener can be attached to the anchor 72, the surgical instrument 10 or both, to help retain the anchor 72 and the buttress 74 on the instrument 10. For example, the fastener can be an aglet or crush ring or clip attached to the anchor 72 at a location adjacent the notch 56.

The buttress fixation system 70 allows the buttress 74 to be released from the stapler 10 so that the stapler 10 can be removed from the site. The staple pusher 64 has a plurality of pushers or fingers 65, each of which extend into the staple receiving slots 52 to eject the staples 50. The fingers 65 have a shape that corresponds to the shape of the staple receiving slot 52. The fingers 65 that are disposed in the staple receiving slot or slots 52 that has the notch 56 have a corresponding protrusion or extension 67 that is disposed in the notch 56. As the staple pusher 64 is advanced, the fingers 65 advance, and the finger or fingers 65 that has the extension 67 will push the length of suture 72, strap, or the like, from the notch 56.

In any of the embodiments disclosed herein, the buttress itself can be made from a variety of biologically compatible materials, and can be made of the same material as the anchor. In certain preferred embodiments, the buttress material is a bio-absorbable material such as polyglycolic acid, glycolide trimethylene carbonate copolymer, polylactic acid, glycolide dioxanone and trimethylene carbonate copolymer, blends and copolymers or any of the bio-absorbable materials used to make sutures, buttresses, and other medical implants. Non-absorbable materials can be used such as polypropylene or polyester. The buttress can be made from animal derived materials, which are known in the art. For example, the buttress material can be made from porcine or bovine tissue, such as porcine dermal collagen, collagen from bovine pericardium, or other materials. The buttress can be made by extrusion, felting, knitting or braiding, molding, non-woven techniques such as melt blown or spun bonding methods, or other methods. The buttress can be porous or non-porous. The buttress can be a foam or mesh. The buttress can have layers of different materials or be some other form of composite material. The buttress material can be made as described in U.S. patent application Ser. No. 13/293,215, filed on Nov. 10, 2011, now U.S. Patent Publication No. 2013-0123816, the entire disclosure of which is hereby incorporated by reference herein.

In any of the embodiments disclosed herein, the buttress 74 has a shape that discourages buckling or wrinkling of the buttress 74. For example, the buttress 74 shown in FIG. 3 has slits 75 extending from the outer edge 76 thereof. Other slits or openings in the buttress 74 may be provided. The buttress 74 has a hole in its middle for allowing the shaft of the stapler 10 to pass through.

Figure 4:
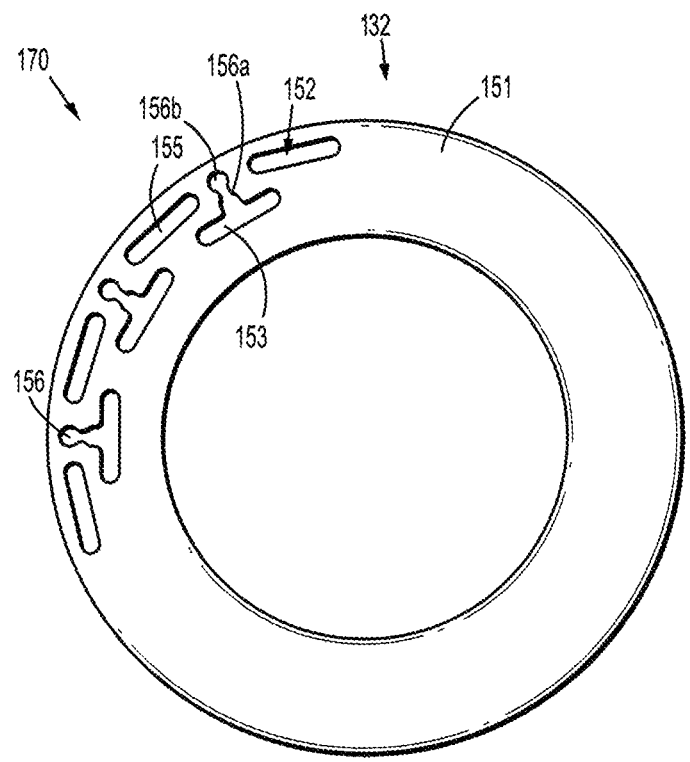
FIG. 4 is a top plan view of a staple cartridge, and a detailed view of a portion thereof, in accordance with an embodiment of the present disclosure.

In a further embodiment shown in FIG. 4, the circular stapling instrument 10 has two rows of staple receiving slots 152. The staple cartridge 132 has a tissue contacting surface 151 that defines an inner row 153 and an outer row 155 of staple receiving slots 152. Although only seven staple receiving slots 152 are shown in FIG. 4, it is understood that the slots 152 extend all the way around the tissue contacting surface 151 of the stapler 10. At least one of the staple receiving slots 152 in the inner row 153 has a notch 156 for the receipt of an anchor, length of suture, strap, wire etc 72, as described above in connection with FIGS. 2A and 3. The notch 156 has a first portion 156a and second portion 156b, as described above in connection with FIG. 2A. This buttress fixation system 170 allows the buttress 74 to be released from the stapler 10 so that the stapler 10 can be removed from the site. The stapler 10 is otherwise arranged as discussed above in connection with FIGS. 1 through 3. The staple pusher, such as staple pusher 64, is a conical member that is advanceable to eject the staples 50 from the slots 152, and has a plurality of pushers or fingers 65, each of which extend into the staple receiving slots 152. The fingers 65 have a shape that corresponds to the shape of the staple receiving slot 152. The fingers 65 that are disposed in the staple receiving slot or slots 152 that has the notch 156 have a corresponding extension 67 that is disposed in the notch 156. As the staple pusher 64 is advanced, the fingers 65 advance, and the finger or fingers 65 that has the extension 67 will push the length of suture, strap, or the like 72, from the notch 156. The buttress 74 may be as shown in FIG. 3, or it may be any generally circular buttress, formed from any of the materials described above. The anchor 72 is disposed in the notch 156 to retain the buttress 74 on the stapler 10, and can be attached to the buttress 74, or the stapler 10, as discussed above in connection with FIG. 3.

FIGS. 2A and 4 show the tissue contacting surface 51 or 151, and only one section of staple receiving slots 52 or 152. In certain embodiments, the buttress fixation system 70 or 170 has twelve staple receiving slots 52 or 152 distributed along the tissue contacting surface 51 or 151 and have the notch 56 or 156. More or fewer such notches 56 or 156 can be provided to securely attach the buttress 74 to the stapling instrument 10.

Figure 5:
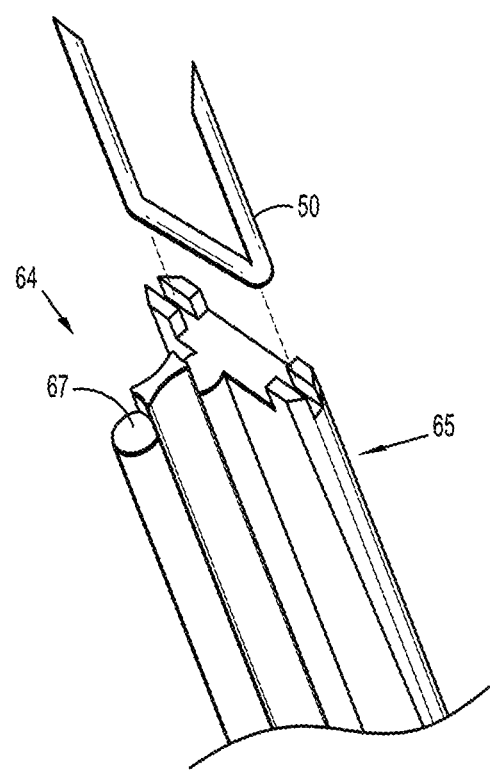
FIG. 5 is a perspective view of a pusher member in accordance with an embodiment of the present disclosure.

One of the fingers 65 of the staple pusher 64 is shown in FIG. 5, and includes the protrusion 67 for pushing the anchor 72 out of the notch 156. In any of the embodiments disclosed herein, the stapler 10 includes one or more staple pushers 64 for ejecting the staples 50 from the staple receiving row slots 52, 152 and has a finger 65 that correspond to each of the slots 52, 152. The fingers 65 that correspond to the slots 52, 152 that have the notch 56, 156 for retaining the anchor 72 have protrusions 67 for pushing the anchor 72 out of the slot 52, 152.

Figure 6:
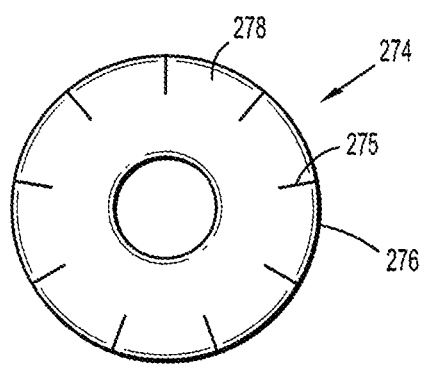
FIG. 6 is a top plan view of a buttress with an outer edge in accordance with another embodiment of the present disclosure.

As shown in FIG. 6, the buttress fixation system 70, 170 may be as described above in connection with FIGS. 1 through 5, with anchors 72 for retaining the buttress 274. The buttress 274 itself includes tabs 278 at the outer edge 276 of the buttress 274, which can be formed by providing slits 275 extending from the outer edge of the buttress 274, or by forming tabs 278 that extend outwardly from the outer edge 276. Tabs 278 may also be formed so as to extend from the lower surface of the buttress 274, adjacent an inner row or outer row of slots. The tabs 278 are arranged to extend into at least some of the staple receiving slots, such as slots 152 or 52 of FIGS. 2 and 4, and an anchor 72 extends into the notch associated with at least some of the slots, such as notches 156 or 56. In this way, the anchor 72 frictionally retains the buttress 274 onto the stapler 10, by engaging the tab 278 of the buttress 274. In any of the embodiments disclosed herein, the buttress fixation system 70, 170 includes a buttress 274 with tabs 278, anchors 72, or both, for releasably retaining the buttress 274.

In any of the embodiments disclosed herein, the tissue contacting surface of the staple cartridge and/or the tissue contacting surface of the anvil member, has a stepped or tapered cross-sectional shape. Desirably, one or more rows of staple receiving slots 52 are defined in a surface that has a different height than the surface in which one or more other rows of staple receiving slots are defined. In addition, in any of the embodiments disclosed herein, the size of the staples in certain of the staple receiving slots may be different than the size of the staples in other of the staple receiving slots. For example, the inner row of staples can be smaller in size (such as leg length) than the outer row of staples (which has a greater leg length) or, if there are three rows of staple receiving slots, the inner row of staples cam be smaller than the middle row of staples and the outer row of staples.

In any of the embodiments disclosed herein, the staple receiving slots can have a curved or angled shape. This allows the staple receiving slots to be positioned more closely to one another in the staple cartridge and/or anvil. The staple forming recesses on the anvil member can have a corresponding shape so that the recesses can be more closely positioned with respect to one another on the anvil member. The staples desirably have a corresponding shape.

Although circular stapling instruments are described above, the stapling instrument could have rows of staples, staple forming recesses, and staple receiving slots that do not define a full circle, but rather a semi-circular, oval, or semi-oval shape. The stapling instrument could have rows of staples, staple forming recesses, and staple receiving slots that form some other shape, such as various polygonal shapes, or partially polygonal shapes. While the present invention has been described in several embodiments, it is not the intention to restrict or in any way limit the scope of the appended claims. Additional advantages and modifications may readily appear to those skilled in the art.

What is claimed is:

1. A stapling instrument comprising:
   a staple cartridge including a tissue contacting surface having a plurality of staple receiving slots defined therethrough, each of the plurality of staple receiving slots including a staple disposed therein, at least one staple receiving slot of the plurality of staple receiving slots including a notch defined through the tissue contacting surface and extending radially outwardly from a portion of the at least one staple receiving slot housing the staple, the notch including a first portion having a first dimension and a second portion having a second dimension larger than the first dimension, the first portion positioned between the second portion and the at least one staple receiving slot; and
   a buttress including a body portion positioned on the tissue contacting surface of the staple cartridge and at least one anchor attached to the body portion, the at least one anchor extending into the notch and positioned laterally adjacent the portion of the at least one staple receiving slot housing the staple, the at least one anchor releasably retaining the buttress to the staple cartridge.

2. The stapling instrument according to claim 1, wherein the plurality of staple receiving slots are arranged in at least two annular rows including an inner row and an outer row, and the at least one staple receiving slot which includes the notch is in the inner row.

3. The stapling instrument according to claim 1, wherein the plurality of staple receiving slots are arranged to include an inner row, a middle row, and an outer row, and the at least one staple receiving slot which includes the notch is in the middle row.

4. The stapling instrument according to claim 1, wherein the anchor is a strap, a cable, a wire, a thread, or a strand.

5. The stapling instrument according to claim 1, wherein the anchor is a suture.

6. The stapling instrument according to claim 1, wherein the anchor is cinched within the notch.

7. The stapling instrument according to claim 1, wherein the anchor has a cross-sectional dimension smaller than the first dimension of the first portion of the notch and is positioned through the first and second portions of the notch such that the notch is cinched within the first portion.

8. The stapling instrument according to claim 1, wherein the anchor of the buttress is disposed laterally adjacent to the staple disposed within the at least one staple receiving slot which includes the notch.

9. The stapling instrument according to claim 8, wherein the staple cartridge includes a staple pusher having a plurality of fingers disposed within the plurality of staple receiving slots, at least one finger of the plurality of fingers that is disposed in the at least one staple receiving slot which includes the notch having an extension extending laterally outwardly from the at least one finger and disposed in the notch.

* * * * *